United States Patent
Dias Júnior et al.

(10) Patent No.: US 10,357,164 B2
(45) Date of Patent: Jul. 23, 2019

(54) METHOD AND DEVICE FOR NON-INVASIVE BLOOD PRESSURE MEASUREMENT

(71) Applicant: ECOLE POLYTECHNIQUE FEDERALE DE LAUSANNE (EPFL), Lausanne (CH)

(72) Inventors: Alair Dias Júnior, Lausanne (CH); Srinivasan Murali, Lausanne (CH); Francisco Javier Rincon Vallejos, Renens (CH); David Atienza Alonso, Echandens (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 43 days.

(21) Appl. No.: 15/305,660

(22) PCT Filed: Apr. 22, 2015

(86) PCT No.: PCT/IB2015/052932
§ 371 (c)(1),
(2) Date: Oct. 21, 2016

(87) PCT Pub. No.: WO2015/162566
PCT Pub. Date: Oct. 29, 2015

(65) Prior Publication Data
US 2017/0042434 A1 Feb. 16, 2017

(30) Foreign Application Priority Data
Apr. 24, 2014 (WO) .................. PCT/IB2014/060978

(51) Int. Cl.
*A61B 5/02* (2006.01)
*A61B 5/021* (2006.01)
(Continued)

(52) U.S. Cl.
CPC ...... *A61B 5/02125* (2013.01); *A61B 5/02416* (2013.01); *A61B 5/02438* (2013.01);
(Continued)

(58) Field of Classification Search
CPC ......... A61B 5/021; A61B 5/00; A61B 5/0404; A61B 5/0408; A61B 5/0456;
(Continued)

(56) References Cited

U.S. PATENT DOCUMENTS 5,316,008 A 5/1994 Suga et al.
9,408,542 B1 * 8/2016 Kinast ................ A61B 5/02125
(Continued)

FOREIGN PATENT DOCUMENTS

EP 2666409 A1 11/2013
WO WO1985003211 A1 8/1985
WO WO 2012/085841 * 6/2012 ............... A61B 5/04

OTHER PUBLICATIONS

Puke, S., Suzuki, T., Nakayama, K., Tanaka, H., & Minami, S. (Jul. 2013). Blood pressure estimation from pulse wave velocity measured on the chest. In 2013 35th Annual International Conference of the IEEE Engineering in Medicine and Biology Society (EMBC) (pp. 6107-6110). IEEE.
(Continued)

*Primary Examiner* — Eric J Messersmith
(74) *Attorney, Agent, or Firm* — Bejin Bieneman PLC

(57) ABSTRACT

A system for measuring blood pressure of a user that comprises an ElectroCardioGram (ECG) circuit with at least two ECG electrodes configured to obtain an electrical activity of a heart of the user by measuring the electrical signals detected at the at least two ECG electrodes as an electrocardiogram waveform, and a pulse oximeter circuit configured to obtain a pulse waveform corresponding to a blood flow on user's vessels. The system further comprises a
(Continued)

processor that is in electrical contact with the electrocardiogram circuit and the pulse oximeter circuit. The processor is configured to simultaneously analyze the electrocardiogram waveform and the pulse waveform. The processor is further configured to identify a "Zero Voltage Crossing" point on the electrocardiogram waveform and to determine time delays from this point to respective different determined points of the pulse waveform; and to use the time delays to compute the blood pressure values.

22 Claims, 7 Drawing Sheets

(51) Int. Cl.
| | |
|---|---|
| A61B 5/024 | (2006.01) |
| A61B 5/0452 | (2006.01) |
| A61B 5/0404 | (2006.01) |
| A61B 5/0408 | (2006.01) |
| A61B 5/0456 | (2006.01) |
| A61B 5/0472 | (2006.01) |
| A61B 5/1455 | (2006.01) |
| A61B 5/1495 | (2006.01) |
| A61B 5/00 | (2006.01) |

(52) U.S. Cl.
CPC .......... *A61B 5/0404* (2013.01); *A61B 5/0452* (2013.01); *A61B 5/0456* (2013.01); *A61B 5/0472* (2013.01); *A61B 5/04085* (2013.01); *A61B 5/1495* (2013.01); *A61B 5/14552* (2013.01); *A61B 5/681* (2013.01)

(58) Field of Classification Search
CPC ... A61B 5/0472; A61B 5/1455; A61B 5/1495; A61B 5/02125; A61B 5/02416; A61B 5/02438; A61B 5/0452; A61B 5/14552; A61B 5/681
See application file for complete search history.

(56) References Cited

U.S. PATENT DOCUMENTS

| | | | |
|---|---|---|---|
| 2005/0096557 A1* | 5/2005 | Vosburgh | A61B 5/02125 600/509 |
| 2007/0021676 A1* | 1/2007 | Han | A61B 5/0404 600/509 |
| 2008/0249382 A1 | 10/2008 | Oh et al. | |
| 2009/0216132 A1 | 8/2009 | Orbach | |
| 2010/0081946 A1* | 4/2010 | Garudadri | A61B 5/0002 600/485 |
| 2011/0009754 A1* | 1/2011 | Wenzel | A61B 5/0215 600/485 |
| 2012/0203077 A1* | 8/2012 | He | A61B 5/02055 600/301 |
| 2016/0354027 A1* | 12/2016 | Benson | A61M 21/02 |

OTHER PUBLICATIONS

Yoon, Y., Cho, J. H., & Yoon, G. (2009). Non-constrained blood pressure monitoring using ECG and PPG for personal healthcare. Journal of medical systems, 33(4), 261-266.

Cohen, A., & Kovacevic, J. (1996). Wavelets: The mathematical background. In Proc. IEEE.

International Search Report (ISR) of the parent application PCT/IB2015/052932 dated Jul. 22, 2015.

Li, C., Zheng, C., & Tai, C. (1995). Detection of ECG characteristic points using wavelet transforms. IEEE Transactions on biomedical Engineering, 42(1), 21-28.

Liu, Z., Wang, J., & Liu, B. (May 2011). ECG signal denoising based on morphological filtering. In Bioinformatics and Biomedical Engineering,(iCBBE) 2011 5th International Conference on (pp. 1-4). IEEE.

Mallat, S., & Zhong, S. (1992). Characterization of signals from multiscale edges. IEEE Transactions on pattern analysis and machine intelligence, 14(7), 710-732.

Mavrilas, D., Tsapikouni, T., Mikroulis, D., Bitzikas, G., Didilis, V., Tsakiridis, K., . . . & Bougioukas, G. (2002). Dynamic mechanical properties of arterial and venous grafts used in coronary bypass surgery. Journal of Mechanics in Medicine and Biology, 2(03n04), 329-337.

Oppenheim, A. V., & Schafer, R. W. (2010). Discrete-time signal processing. Pearson Higher Education.

Rincon, F., Recas, J., Khaled, N., & Atienza, D. (2011). Development and evaluation of multilead wavelet-based ECG delineation algorithms for embedded wireless sensor nodes. IEEE Transactions on Information Technology in Biomedicine, 15(6), 854-863.

Sun, Y., Chan, K. L., & Krishnan, S. M. (2005). Characteristic wave detection in ECG signal using morphological transform. BMC cardiovascular disorders, 5(1), 1.

Written Opinion of the International Search Authority of the parent application PCT/IB2015/052932 dated Jul. 22, 2015.

* cited by examiner

METHOD AND DEVICE FOR NON-INVASIVE BLOOD PRESSURE MEASUREMENT

CROSS REFERENCE TO RELATED APPLICATIONS

The present application is a U.S. national stage application of PCT/IB2015/052932 filed on Apr. 22, 2015 designating the United States, and claims foreign priority to International patent application PCT/IB2014/060978 filed on Apr. 24, 2014, the contents of both documents being herewith incorporated by reference in their entirety.

FIELD OF THE INVENTION

The invention relates to determining blood pressure by analyzing the ElectroCardioGram (ECG) and pulse waveforms.

1 INTRODUCTION

There is a strong need for Non-Invasive continuous measurement of Blood Pressure (NIBP) to monitor, diagnose and follow-up patients and healthy persons as well. Most common NIBP methods are based on mechanical or oscillometric recordings: they require a cuff to be placed on the upper arm or wrist and involve application of pressure on the cuff. Moreover, they cannot be used to obtain continuous beat-to-beat (heart of pulse beat) recording of blood pressure changes, as there is a gap of 2-3 minutes required between subsequent recordings. Recently, novel ways of measuring the blood pressure from a combination of multiple sensors have been developed. The most promising ones use a combination of readings from at least three sensing systems: ElectroCardioGram (ECG), Pulse Oximeter or PhotoPlethysmoGram (PPG, or Pleth), and either phonocardiogram or Impedance Cardiogram (ICG). Most of these methods are based on measuring the time differences between the different waveforms of ECG, PPG and ICG or phonocardiogram and relating them to the blood pressure changes.

The ECG device records the electrical activity of the heart that is detected by two or more electrodes on the device. It records the electrical impulses produced by the polarization and depolarization of tissues in the heart.

The pulse oximeter measures the oxygen saturation level (SpO2). A PPG device is a pulse oximeter that uses optical technique to measure the change in the volume of arterial blood with the pulse beat. The device usually measures the change in blood volume at peripheral body parts, typically on fingertips.

In ICG, current is transmitted through the chest of the subject and the change in impedance of current passing through the heart, based on the blood flow changes in the aorta, is measured. In phonocardiogram, the sound from the heartbeats is recorded. While ECG and PPG can be measured at different parts of the body (such as the chest, hands, ears, etc), in order to accurately track the ICG or phonocardiogram, the recordings need to be performed close to the chest.

From the sensor recordings, the Pulse Transit Time (PTT): the time difference between the R peak of the ECG and the peak of pulse wave, and the Pre-ejection Period (PEP): the time difference between the R peak of the ECG and the peak of ICG or phonocardiogram are measured. The blood pressure changes are then estimated from the PTT and PEP values for each beat.

One goal of the present invention is to provide a method and a device to measure continuously non-invasively blood pressure from advanced features of the ECG and PPG only. We also present a wrist worn device for acquiring the ECG and PPG, which further computes the blood pressure.

SUMMARY OF THE INVENTION

In a first aspect, the invention provides a wrist-worn device for measuring blood pressure of a user, intended to be wrist worn. The wrist-worn device comprises a back dial and/or a back side of a strap of the wrist-worn device configured to be in contact with a user's arm on which the device is intended to be worn. The wrist-worn device further comprises at least an ElectroCardioGram (ECG) circuit with at least two electrodes configured to obtain an electrical activity of a heart of the user by measuring electrical signals detected at the at least two electrodes, and a pulse oximeter circuit configured to obtain a pulse waveform corresponding to a blood flow on user's vessels. One or more of the at least two ECG electrodes is placed on the back dial and/or on the back side of the strap, and one or more of the at least two ECG electrodes is placed on a front side of the device or on a front side of the strap and is configured to be touched. The pulse oximeter further comprises an optical sensor functionally connected to the pulse oximeter, the optical sensor being placed either on the back dial and/or the back side of the strap, or on the front side of the device or on the front side of the strap in a proximity of the one or more of the at least two ECG electrodes. The proximity is configured such that an intended touch by the user of the one or more of the at least two ECG electrodes causes the corresponding optical sensor to be also touched, and whereby the Electrocardiogram circuit and the pulse oximeter are configured to simultaneously measure the ECG waveform and pulse oximeter waveform and the device comprises computing means configured to use the waveforms and compute blood pressure.

In a second aspect, the invention provides a system for measuring blood pressure of a user that comprises an ElectroCardioGram (ECG) circuit with at least two ECG electrodes configured to obtain an electrical activity of a heart of the user by measuring the electrical signals detected at the at least two ECG electrodes as an electrocardiogram waveform, and a pulse oximeter circuit configured to obtain a pulse waveform corresponding to a blood flow on user's vessels. The system further comprises a processor that is in electrical contact with the electrocardiogram circuit and the pulse oximeter circuit. The processor is configured to simultaneously analyze the electrocardiogram waveform and the pulse waveform. The processor is further configured to identify a "Zero Voltage Crossing" point on the electrocardiogram waveform and to determine time delays from this point to respective different determined points of the pulse waveform; and to use the time delays to compute the blood pressure values.

In a third aspect, the invention provides a method for measuring blood pressure. The method comprises steps of analyzing an electrocardiogram waveform and a pulse waveform obtained from an electrocardiogram circuit and a pulse oximeter circuit; identifying a "Zero Voltage Crossing" point on the electrocardiogram waveform and determining time delays from this point to different determined points of the pulse waveform; and calculating the blood pressure based on a function of the time delays.

In a preferred embodiment, an effective time delay $T_{eff}$ is measured from the "Zero Voltage Crossing" point to a steepest point of the pulse wave.

In a further preferred embodiment an effective time delay $T_{eff}$ is measured from the "Zero Voltage Crossing" point to a peak of the pulse wave.

In a further preferred embodiment the electrocardiogram waveform and the pulse waveform are offset by one or more electrocardiogram beats from each other.

In a further preferred embodiment the electrocardiogram waveform and the pulse waveform are offset by one or more electrocardiogram beats from each other.

In a further preferred embodiment the electrocardiogram waveform and the pulse waveform are offset by one or more electrocardiogram beats from each other.

In a further preferred embodiment the electrocardiogram waveform and the pulse waveform are offset by one or more electrocardiogram beats from each other.

In a further preferred embodiment multiple electrocardiogram waveform beats are merged into a single beat for analysis, and wherein the merging is an ensemble average of the beats.

In a further preferred embodiment multiple pulse waveform beats are merged into a single beat for analysis, wherein the merging is an ensemble average of the beats.

In a further preferred embodiment computing the "Zero Voltage Crossing" point involves using wavelets as follows: computing a dyadic discrete wavelet transform of the electrocardiogram for different wavelet scales; determining a peak of an R waveform by searching for pairs of maximum moduli of opposite signals across all considered scales that exceed predefined thresholds; determining a peak of an S waveform by searching for pairs of maximum moduli of opposite signals at a chosen scale, chronologically after the peak of the R waveform, but in its neighborhood; and determining the zero-voltage crossing point by searching after a maximum modulus associated to a last slope of a QRS complex at a chosen scale for a value that is lower than a predefined threshold.

In a further preferred embodiment "Zero Voltage Crossing" point is computed using Multiscale Morphological Derivative (MMD) as follows: computing an MMD transform of the electrocardiogram waveform; detecting peaks of R waveforms by searching for minima that exceed a pre-defined threshold value; determining peaks of S waveforms by searching for a first maximum chronologically after the peaks of the R waveforms; and defining the zero-voltage crossing point as a first local minimum chronologically after the peaks of the S waveforms.

In a further preferred embodiment the step of calculating the blood pressure values involves computing based on multiple functions of the time delays from the "Zero Voltage Crossing" point to the pulse waveforms, each one for a specific range of RR intervals of the electrocardiogram waveform, with a particular function chosen based on the corresponding RR interval of the electrocardiogram waveform.

In a further preferred embodiment the method further comprises performing a pre-calibration step of computing the blood pressure values using an existing blood pressure device, along with a simultaneous measurement of the time delays from the "Zero Voltage Crossing" point to the pulse waves, and building an offset function that relates the values, and the offset function is further used to adjust the function mapping the time values and the blood pressure calculations.

In a further preferred embodiment multiple offset functions are computed, each one for a specific range of RR intervals of the electrocardiogram waveform, with a particular function chosen based on the corresponding RR interval of the electrocardiogram waveform.

In a further preferred embodiment the method is applied to more than one lead of the electrocardiogram waveform and the time values are computed as an average of the different values across the different leads.

In a further preferred embodiment the method is applied to a combination of more than one lead of electrocardiogram waveform, with the different leads combined by an averaging function.

In a further preferred embodiment the method is applied to a combination of more than one lead of the electrocardiogram waveform, with the different leads combined by performing a Root Mean Square (RMS) of the leads.

In a further preferred embodiment the electrocardiogram waveform single beat is discarded if the RR interval of the electrocardiogram waveform is outside a pre-defined threshold value.

In a further preferred embodiment the pulse waveform single beat is discarded if the RR interval of the electrocardiogram waveform is outside a pre-defined threshold value.

In a further preferred embodiment, if more than R or S waveform of electrocardiogram waveform is detected at any beat, the beat and corresponding pulse waveforms are discarded when computing the ensemble average.

In a further preferred embodiment, in the intervals between the R peaks, S peaks and the Zero-Voltage Crossing points are also checked to see if they fall within a predefine range, and if not, the corresponding ECG beat and pulse waveforms are discarded when computing the ensemble average.

In a further preferred embodiment, if the time intervals between the Zero-Voltage Crossing point and the different determined points of the pulse waveform do not fall within predefined ranges, the blood pressure computation is not performed and postponed until the processing of a valid window.

In a further preferred embodiment, if the time intervals between the Zero-Voltage Crossing point and the different determined points of the pulse waveform do not fall within predefined ranges, the corresponding ECG beat and pulse waveforms are discarded when computing the ensemble average.

BRIEF DESCRIPTION OF THE DRAWINGS

The invention will be better understood from the description of example embodiments and in light of the figures, wherein.

2. WRIST WORN DEVICE FOR BLOOD PRESSURE MEASUREMENT

Figure 1:
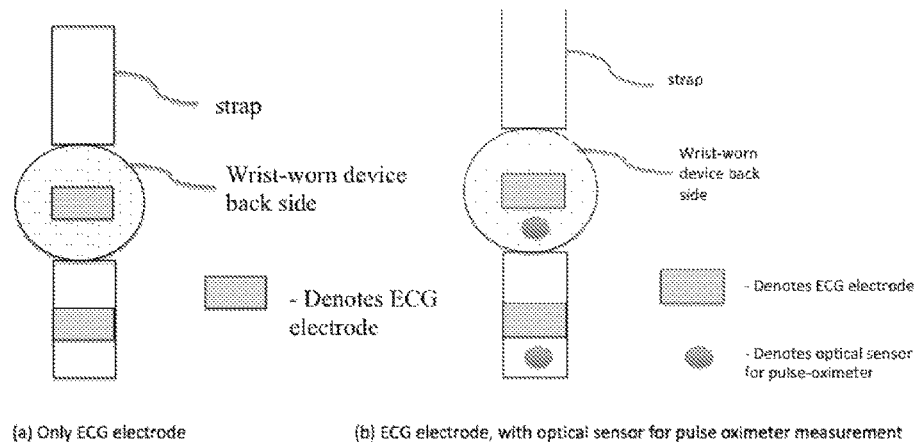
FIG. 1 shows a back side of the wrist worn device. This will be contact with the hand when worn. In one configuration (Figure (a)), only the ECG electrode is placed. In another configuration, along with the ECG electrode, an optical sensor for pulse oximeter measurement is placed as well.

In this patent, we present a wrist worn device and a method for measurement of blood pressure. The wrist-worn device has the following components: two or more electrodes for ECG measurement and one ore more optical sensor for pulse oximeter measurement. One or more of the ECG electrodes is placed either on the back dial of the device or on the strap, such that it's in contact with the arm in which the device is worn. The strap itself could be made of the material of ECG electrode, so that the entire strap (back side in contact with the arm) can even be used for acquisition. The optical sensor could be placed either on the back side of the device, or could be placed on the front face as well. In the former case, the optical measurement is done on the arm on which the device is worn, while in the latter case, the measurement is through the other arm by which the device is touched. In FIG. 1, we show some of the configurations in which the ECG electrode and the optical sensor can be placed on the back side of the device. Please note that the optical sensor need not be placed together with the ECG electrode. The only requirement is that both of them have contact with the arm, for the purpose of signal acquisition.

Figure 2:
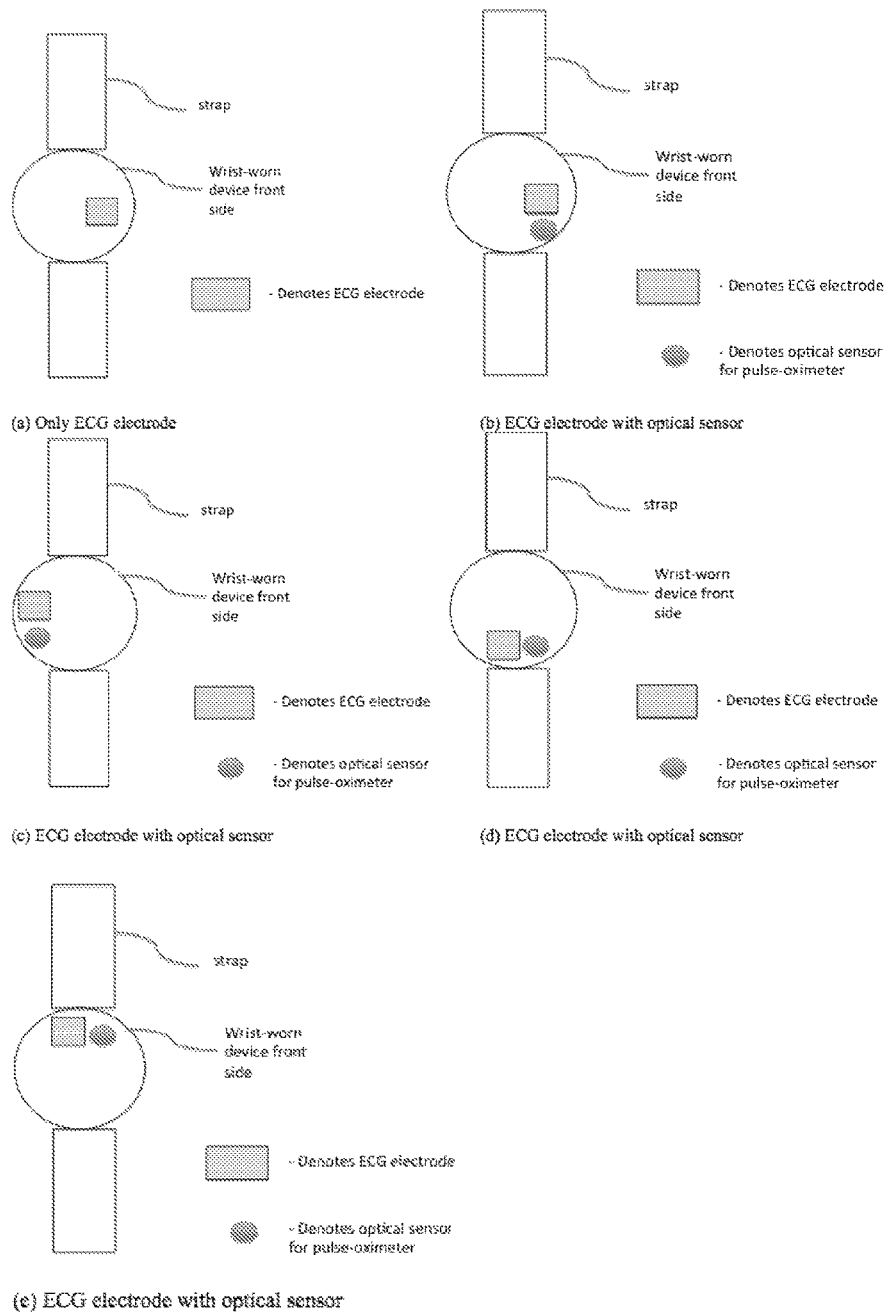
FIG. 2 shows a front side of the wrist worn device. In Figure (a), we show a configuration where only an ECG electrode is used on the front side. In Figures (b)-(e), different configurations are shown when the ECG electrode along with the optical sensor is used.

On the front side of the device, one or more of the ECG electrodes are placed. The user touches the electrode from the other arm (than the one where the device is worn). This allows the ECG signal acquisition across the two different hands, thereby allowing measuring the electrical conduction across the heart. The optical sensor is placed on the front face, such that the user only needs to use one or few fingers to touch both the ECG electrode and the optical sensor at the same time. This allows for a single touch acquisition of ECG and SPO2, which are further used to compute the blood pressure. In FIG. 2, we present the front face of the device. The ECG electrode and/or the optical sensor can be placed either on the front face of the device or on the front face of the strap as well.

3. METHOD FOR CALCULATING BLOOD PRESSURE BEAT-TO-BEAT

In this section, we present a method for measuring the blood pressure from a simultaneous recording of ECG and pulse wave. The ECG and pulse waves can be measured at the wrist, as explained in the previous section. Alternately, for the method to work, the ECG and pulse waves can be measured at different parts of the body as well, such as the chest, fingers, ears, etc.

Please note that even if the ECG is measured at the hand, no significant impact will be perceived on the data acquisition since the transit time of the electrical signal is very fast when compared to the actual flow of blood from the heart to the fingers in the arm.

Figure 4:
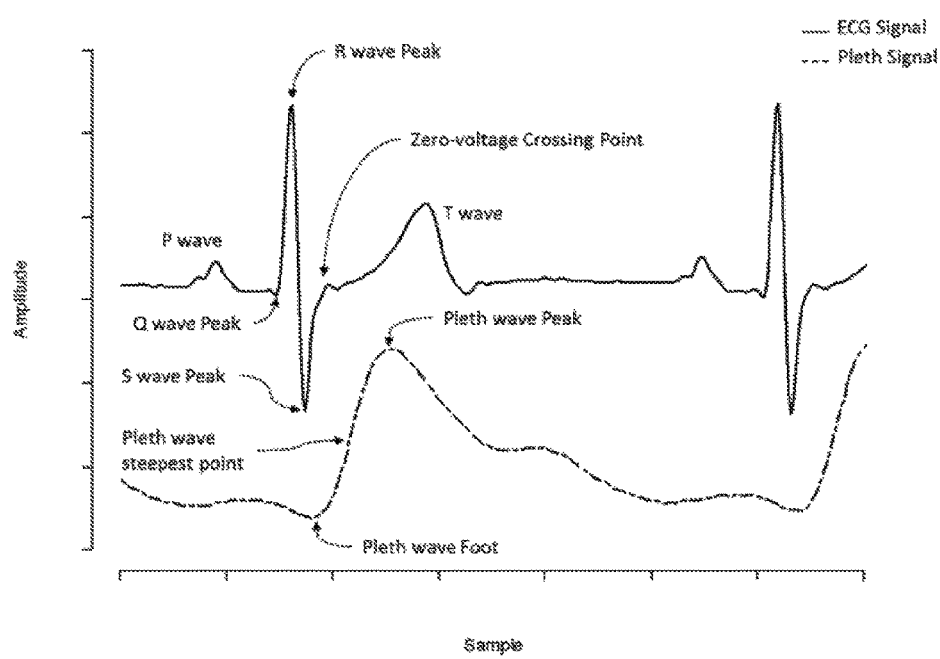
FIG. 4 shows a graph of ECG and pulse signal characteristic points.

The ECG wave for a normal sinus rhythm (healthy person) for a single heartbeat is shown in FIG. 4. The P-wave of ECG corresponds to atrial depolarization (beginning of atrial contraction), QRS complex corresponds to ventricular depolarization (ventricular contraction) and the T-wave corresponds to ventricular repolarization (beginning of ventricular relaxation). After the completion of the QRS complex, we mark the point when the ECG signal crosses the zero voltage as "Zero-voltage Crossing Point", that is associated with the time when the wave of depolarization has completed its passage through the heart. This also marks the time that the blood has left the heart.

In this patent, we determine this Zero-voltage Crossing Point on the ECG and use it to determine the systolic and diastolic blood pressure. We also present a method to determine the point in real-time on the device itself and use it to obtain the blood pressure.

In a beat-to-beat blood pressure estimation scheme, a new ABP value is provided by the system for every complete cardiac period. An internal buffer is used to accumulate samples until a complete cardiac cycle is identified. This signal window is then analyzed in order to obtain an estimation of the ABP.

Figure 3:
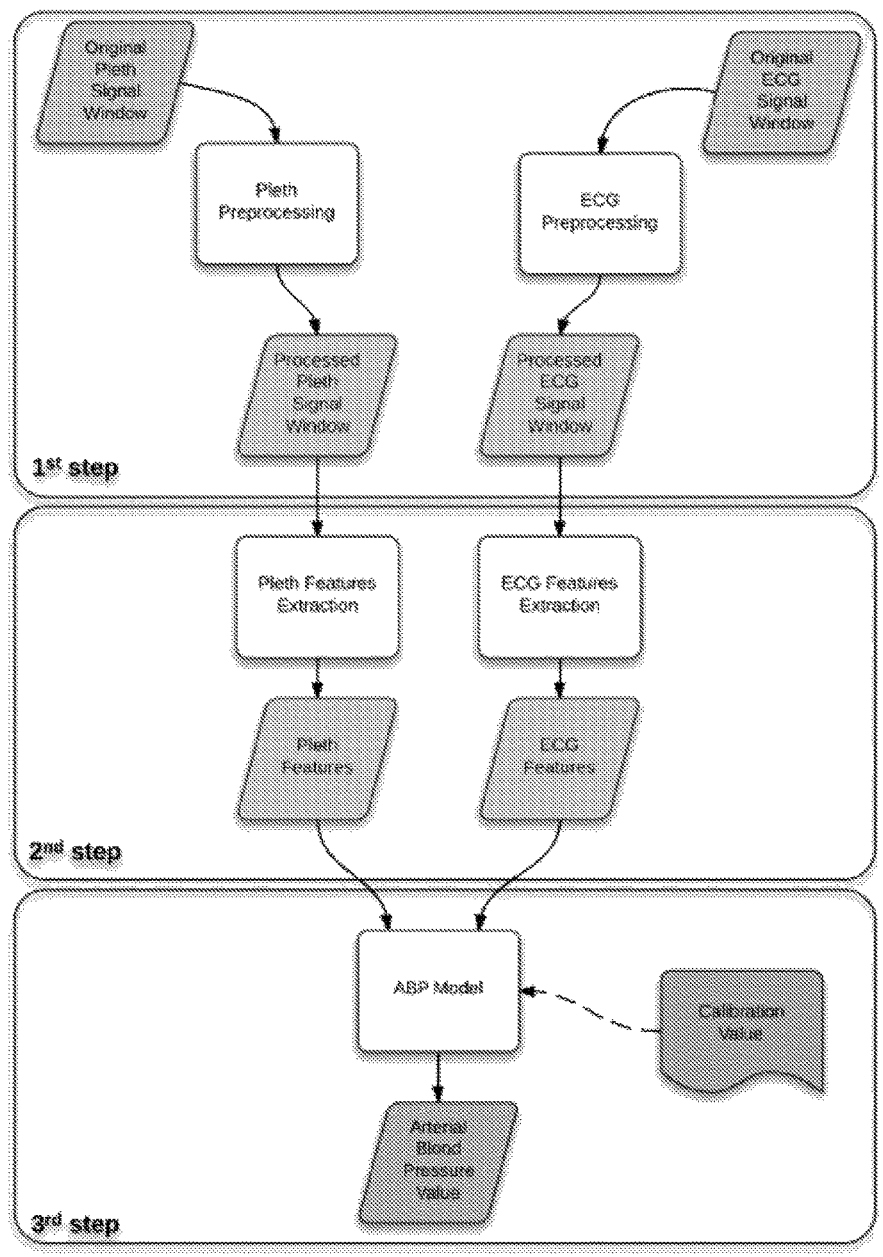
FIG. 3 illustrates an overview of the method according to the invention.

From the signal processing perspective, the ABP calculation method can be better described if divided into 3 major steps, as depicted in FIG. 3. After the acquisition of the involved signals, a preprocessing step is performed on the signal window in order to obtain a better quality signal (first step). This preprocessing step is basically composed of filtering algorithms, notably:

a) Forward-Backward low-pass filtering, for removing high frequency noise;
  b) Forward-Backward high-pass filtering, for removing low frequency noise and off-set;
  c) Morphological filtering, for enhancing the signal characteristic points.

ECG signals are particularly sensitive to different types of noises like motion artifacts, 50/60 Hz interference, and base-line drift caused by respiration [1]. The morphological filtering approach is, therefore, essential to obtain a high quality measurement of the ECG signal characteristic points used to estimate the ABP value.

After the preprocessing step, the characteristic points of the involved signals can be extracted. This is done in the second step of FIG. 3. FIG. 4 graphically shows the Pleth and ECG characteristic points considered for the purposes of this invention. For each one of the characteristic points presented in FIG. 4, both the sample number (x axis) and the amplitude value (y axis) are recorded for future analysis.

In the third step of the method, the ABP model determines the ABP value. The model uses the characteristic points extracted in the second step, in special the Zero-voltage crossing point of the ECG signal and a fixed point on the Pleth wave, to provide an estimation of the actual ABP. To improve the estimation accuracy, an ABP calibration value can be fed to the ABP model. This calibration value is established by means of a one-time ABP determination using conventional methods and should preferably be acquired and provided concomitantly with the acquisition of the ECG and Pleth. After calibrated once, the system does not need to be calibrated for the same person again. However, due to physiological changes, periodic calibrations are recommended.

In the following sections, each of the processes of FIG. 3 are explained in detail.

3.1 Forward-Backward Filters

Filtering the acquired signals is fundamental for correctly extracting the characteristic points depicted in FIG. 4, in special the Zero-voltage Crossing Point of the ECG signal. However, filtering a signal usually incurs in a phase difference between the input and output signals. Sometimes, the filter phase response is non-linear (the phase shift is not directly proportional to the frequency) which may result in distortions that have an impact on the accuracy of the measurement of the characteristic points.

It is possible to create a filter with zero-phase distortions simply by applying the filter over the signal in both the forward and reverse directions [2]. This forward-backward filter scheme has the following characteristics:
 a) Zero-phase response;
 b) Squared amplitude response with respect to the original filter.

Low-pass and high-pass Forward-backward digital filters are employed in the preprocessing step (first step) of both ECG and Pleth signals. The filters are designed using conventional filter design techniques.

3.2 Morphological Filters

Conventional filters can be used to remove noise that present frequency components different from those present in the actual signal, but have difficulties in removing noise with frequency components similar to the signal being filtered. The morphological filtering, on the other hand, provide an effective non-linear way of filtering the signal while keeping its shape good [1]. Morphological filters based on the ones presented in [1] are used in the preprocessing step (first step) of FIG. 3 to remove noise from the ECG signal only. Morphological filters are not applied to the Pleth signal.

3.3 ECG Signal Characteristic Points Extraction

Since the R peak of the ECG is the most prominent feature of the signal waves, the features extractions start with the ECG signal. Once the R peaks are detected, the period of the signals (both ECG and Pleth) is easily determined.

Two techniques were employed to extract the features of the ECG signal, with comparable degrees of success. The first one is a dyadic Discrete Wavelet Transform (DWT) based analysis [3] and the second one is a Multiscale Morphological Derivative (MMD) transform based analysis [4]. For both techniques, the processing is performed over a signal window composed of a small number of heartbeats. Since the thresholds are calculated over a limited amount of time, the locality of the signal is inherently considered for the computations.

3.3.1 Dyadic Wavelet Transform Based Analysis

According to Mallat [5], for discrete-time signals, the dyadic DWT is equivalent to an octave filter bank. Therefore, in the DWT based analysis, we employ the filter-bank implementation using the algorithme à trous presented by [6]. Using this filter-bank, we obtain the DWT representation of the first four wavelet scales (wavelet scale $2^4$ to wavelet scale $2^1$) of the signal. These representations are used to extract the characteristic points of the ECG signal wave.

In order to detect the peak of the R wave, similarly to [7], we search for a pair of maximum moduli lines of opposite signs present across all the wavelet scales and exceeding the predefined thresholds $\in^4$ to $\in^1$, starting at wavelet scale $2^4$. If a maximum modulus is found at wavelet scale $2^4$, then we look for one maximum modulus in its neighborhood at scale $2^3$, and so on for the lower scales. A maximum modulus in wavelet scale $2^k$ is considered to be in the neighborhood of one in wavelet scale $2^{k-1}$ if the interval between them is less than 40 ms. The rules in [3] are used to eliminate redundant lines and to select the most significant pair of maximum moduli. The peak of the R wave is detected as the zero crossing between the two maximum moduli at wavelet scale $2^1$.

Additionally to the said procedures, we also check the consistence of the detection. If the R peak is positive, then the maximum lines at wavelet scale $2^1$ should be a positive peak followed by a negative peak. Conversely, if the R peak is negative, then the maximum lines should be a negative peak followed by a positive peak. If this is not the case, the detected peak is discarded.

The threshold detection values $\in^4$ to $\in^1$ are calculated according to equations 1 and 2.

$$\epsilon^i = \sqrt{\frac{1}{N}\sum_{n=1}^{N} w_{2^i}(n)}, \quad i=1,2,3 \qquad (1)$$

$$\epsilon^4 = \frac{1}{2}\sqrt{\frac{1}{N}\sum_{n=1}^{N} w_{2^4}(n)}, \quad i=1,2,3 \qquad (2)$$

After the main peak of the QRS complex has been detected, the secondary waves around it can be similarly determined. Likewise, the secondary waves peaks are associated with a pair of absolute maximum moduli with opposite signs across the scales. For the purposes of this invention, only the peak of the S wave is taken into consideration. This peak is detected by searching for a pair of maximum moduli lines at wavelet scale $2^2$ exceeding the threshold, $\gamma$, given by equation 3, in a window starting at the R peak and ending 160 ms after it.

$$\gamma = 0.20 \times \max(|w_{2^2}(n)|) \qquad (3)$$

The peak of the S wave is used to detect the zero-voltage crossing point presented in FIG. 4. Let $n_{Last}$ be the maximum modulus at wavelet scale $2^4$ associated to the last significant slope of the QRS complex (usually the last maximum modulus identified during the search for the S wave peak at wavelet scale $2^2$). Looking at the wavelet scale $2^4$, the zero-voltage crossing point is the first sample after $n_{Last}$ whose value is lower than $\alpha_z$. The threshold $\alpha_z$ is calculated according to the Equation 4.

$$\alpha_z = 0.7 \times |w_{2^4}(n_{max})| \qquad (4)$$

where $n_{max} = \arg_n \max|w_{2^4}(n)|$, $n \in [n_{Last}+1; n_{Last}+s]$ and s is the number of samples corresponding to 40 ms.

When the S wave is missing or is not detected for some reason, the last slope of the R wave is used for determining $n_{Last}$.

3.3.2 Multiscale Morphological Derivative Transform Based Analysis

An alternative way of determining the characteristic points depicted in FIG. 4 is to use Multiscale Morphological Derivative Transform. MMD based analysis is more robust than DWT based analysis with respect to the value of the constants used to calculate the thresholds. Besides, due to the nonlinearity of the morphological transform, the problem of position deviation faced by DWT based techniques can be avoided [4] and, as a result, crossing across the scales is not required. On the other hand, the MMD transform approach requires the morphology of the ECG signal to be known a priori. This limitation makes it difficult to use MMD transform in ECG signals from patients affected by arrhythmias, but it is not a problem in processing ECG signals from healthy subjects.

The formula presented in equation 5 [4] was used to calculate the MMD transform of the signals.

$$M_f^{d_s}(x) = (\max(f(t)))_{t \in [x-s, x+s]} + \min(f(t))_{t \in [x-s, x+s]} - 2 \times f(x) \quad (5)$$

Where f(x) is the signal being transform, s is the MMD scale value, and $M_f^{d_s}(x)$ is the value of the MMD transform of f(x) at MMD scale s.

In this text, we only describe the procedure to extract the features of the ECG lead II. Similar analysis can be done to the other leads. The peaks of the R waves are detected by searching for minima in $M_{fECG}^{d_{20}}(x)$ that exceed the threshold value defined by equation 6. The histogram approach for calculating the threshold proposed in [4] is not necessary in this case, due to the limited length of the analysis window.

$$\in_R = 0.8 \times \min(M_{fECG}^{d_s}(x)) \quad (6)$$

After the detection of the R wave peak, the S wave peak is detected. The first maximum to the right of the point in $M_{fECG}^{d_{20}}(x)$ associated to the peak of the R wave is the marked as the peak of the S wave. The next local minimum to the right of the point in $M_{fECG}^{d_{20}}(x)$ associated to the peak of the S wave is the Zero-voltage crossing point depicted in FIG. 4.

3.4 Pleth Signal Characteristic Points Extraction

The extraction of the Pleth characteristics in the beat-to-beat ABP estimation scenario uses the MMD transform, described by equation 5. The Pleth wave steepest points depicted in FIG. 4 are detected by searching for zero crossing points in $M_{fpleth}^{d_{30}}(x)$. The peak of the pleth wave is the minimum point between two zero-crossing points of $M_{fpleth}^{d_{30}}(x)$ and the foot of the pleth wave is the maximum point between two zero-crossing points of $M_{fpleth}^{d_{30}}(x)$.

3.5 ABP Estimation Model

Figure 5:
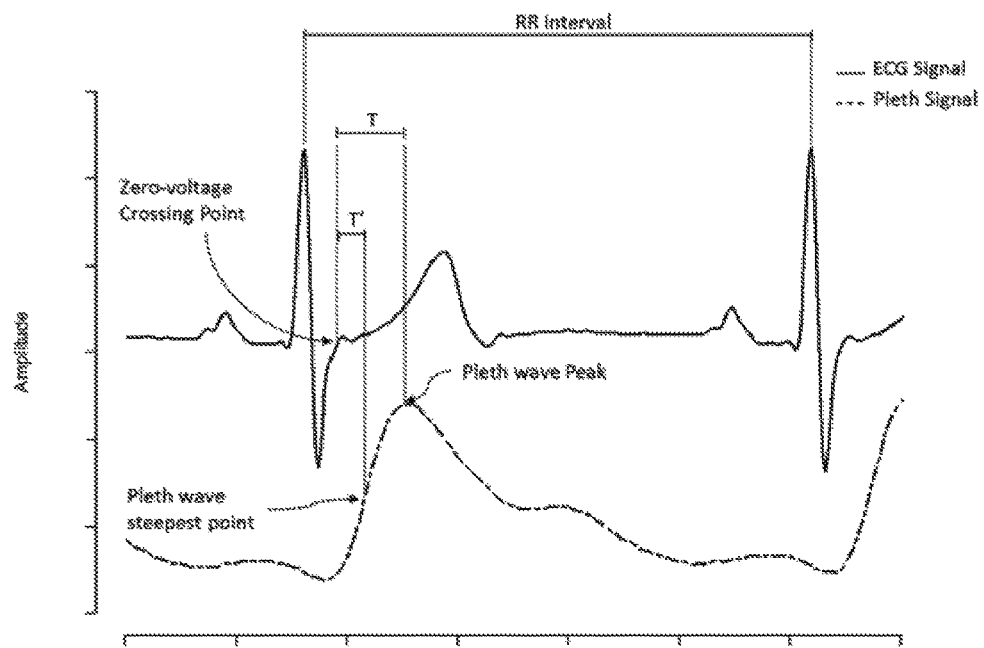
FIG. 5 contains a graph illustrating intervals used in the ABP model.

The ABP estimation model of the third step of FIG. 3 takes as inputs the characteristic points extracted during the features extraction process of the second step of the method. These characteristic points are used to calculate the intervals used by the model to determine the current value of the arterial blood pressure. The intervals used in this invention are:

a) $T_{eff}$—The interval between the Zero-voltage crossing point of the ECG signal and a fixed point of the corresponding Pleth wave;
b) RR—The interval between the R peaks of two consecutive heartbeats;

A graphical representation of these intervals is given in FIG. 5. As examples, two possibilities are considered for the calculation of $T_{eff}$ in that figure: the interval between the zero-voltage crossing point and the peak of the Pleth wave (T); and the interval between the zero-voltage crossing point and the steepest point of the Pleth wave (T'). Any other well defined characteristic point on the Pleth wave may be used to calculate this interval.

During the research, each of the aforementioned intervals have shown a significant crossed-correlation with the values of the systolic, diastolic and mean arterial blood pressure (MAP) and can be used to create a model to calculate any of these three variables. Three approaches were considered to construct the ABP estimation models.

The first one is a univariable one-time calibration method that works on a single hypothesis over the relationship between the calculated intervals and the values of the ABP. Experimental data obtained from several subjects that were submitted to different levels of activity is used to create a regression model, $f^{type}$. The model itself can be created using any regression technique described in the literature, in special polynomial curve fitting and exponential curve fitting. This model represents the general relationship between the pressure value and the considered time interval ($T_{eff}$). The uncalibrated pressure values are determined as presented in equations 7 to 9.

$$P_{unc}^{Syst} = f^{Syst}(T_{eff}) \quad (7)$$

$$P_{unc}^{Diast} = f^{Diast}(T_{eff}) \quad (8)$$

$$P_{unc}^{Map} = f^{map}(T_{eff}) \quad (9)$$

In order to obtain the actual pressure value for an individual, given the $T_{eff}$ interval, it is executed a one-time calibration step. The calibration step is performed only once by acquiring concomitantly the ECG, Pleth and pressure value. The pressure value can be determined using any conventional pressure determination method. After the calibration procedure, an offset value is obtained and the actual blood pressure values of future measurements can be determined as presented in equations 10 to 12.

$$P^{Syst} = P_{unc}^{Syst} + \text{offset}^{Syst} \quad (10)$$

$$P^{Diast} = P_{unc}^{Diast} + \text{offset}^{Diast} \quad (11)$$

$$P^{Map} = P_{unc}^{Map} + \text{offset}^{Map} \quad (12)$$

Figure 6:
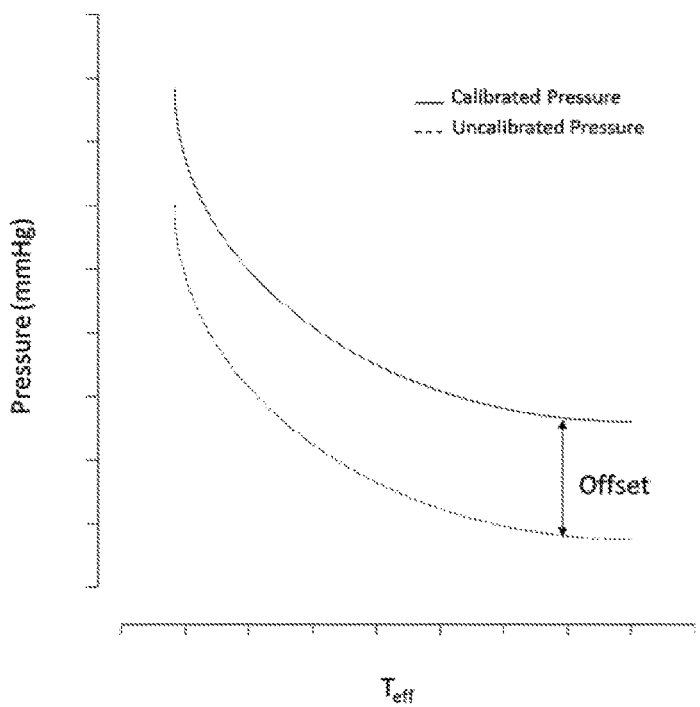
FIG. 6 contains a graph illustrating blood pressure estimation using univariable single hypothesis one-point calibration model.

FIG. 6 qualitatively shows the pressure estimation method based on the one-point calibration single hypothesis model using the offset obtained by the calibration procedure.

The second approach is a multivariable one-point calibration method that works on a single hypothesis over the relationship between the calculated intervals and the values of the ABP. Experimental data, obtained from several subjects that were submitted to different levels of activity, is used to create a regression model, $g^{type}$. The model itself can be created using any regression technique described in the literature, in special polynomial curve fitting and exponential curve fitting. This model represents the general relationship between the pressure value and the considered time intervals ($T_{eff}$ and RR). The uncalibrated pressure values are determined as presented in equations 13 to 15.

$$P_{unc}^{Syst} = g^{syst}(T_{eff}, RR) \quad (13)$$

$$P_{unc}^{Diast} = g^{diast}(T_{eff}, RR) \quad (14)$$

$$P_{unc}^{Map} = g^{Map}(T_{eff}, RR) \quad (15)$$

In order to obtain the actual pressure value for an individual, given the RR and $T_{eff}$ intervals, it is executed a one-point calibration step. The calibration step is performed only once by acquiring concomitantly the ECG, Pleth and pressure value. The pressure value can be determined using any conventional pressure determination method. After the calibration procedure, an offset value is obtained and the actual blood pressure values of future measurements can be determined as presented in equations 10 to 12.

Figure 7:
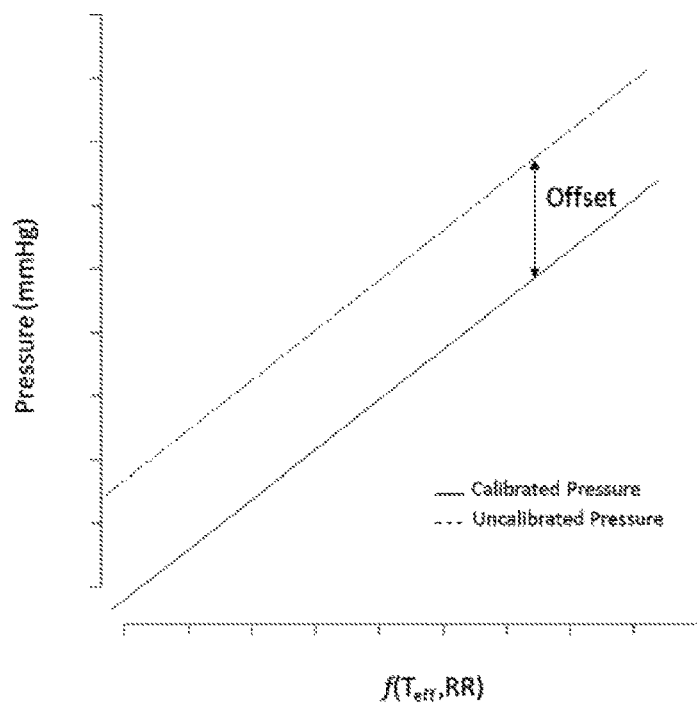
FIG. 7 contains a graph illustrating blood pressure estimation using multivariable single hypothesis one-point calibration model.

FIG. 7 qualitatively shows the pressure estimation method based on the multivariable one-point calibration single hypothesis model using the offset obtained by the calibration procedure.

Figure 8:
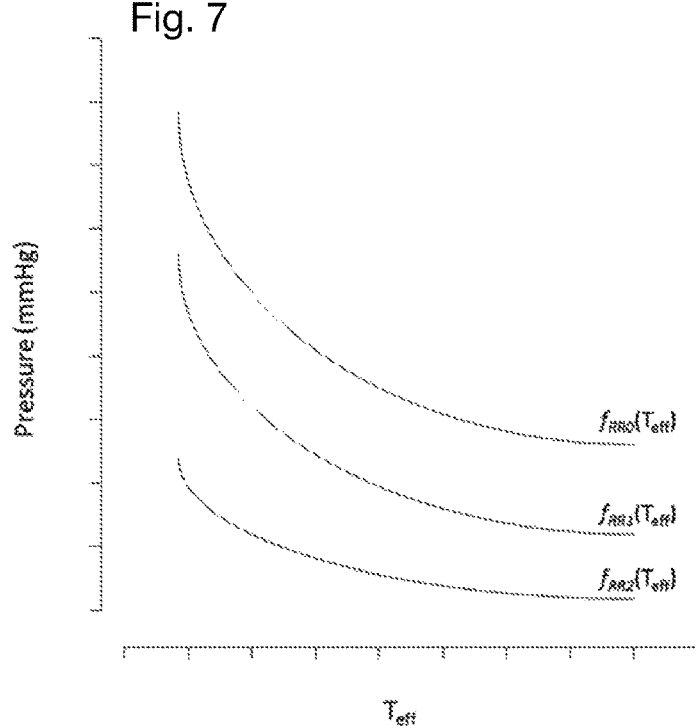
FIG. 8 contains a graph illustrating blood pressure estimation using multivariable multi-hypothesis model.

The third approach considers a dynamic model, where several hypothesis are used to determine the ABP according to the values of the RR interval. This approach is based on results presented by studies showing that the mechanical characteristics of blood vessels depend on the frequency [8]. In this case, the $T_{eff}$ interval is used for the model fitting, as in the first approach, whereas the RR interval is used to change the model itself. FIG. 8 depicts this multi-hypothesis method where the curve used for the ABP estimation changes depending on the value of the RR interval.

Figure 9:
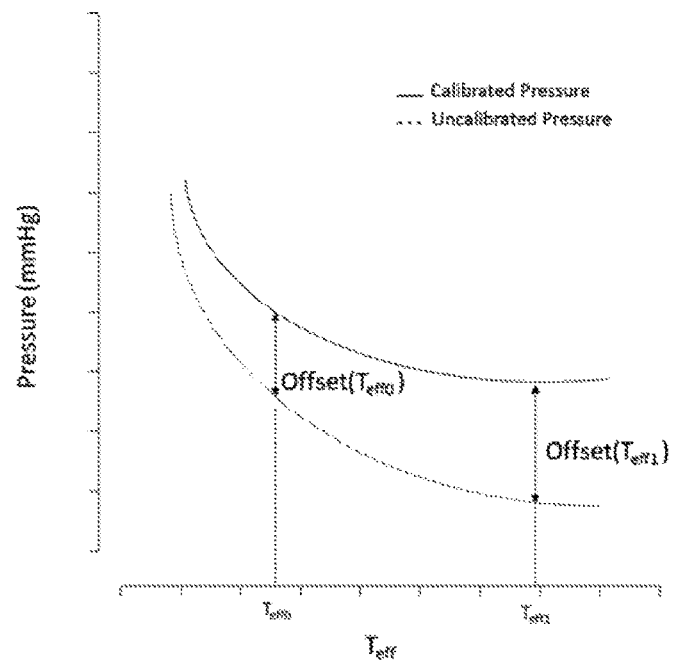
FIG. 9 contains a graph illustrating blood pressure estimation using the univariable single hypothesis multi-point calibration model.
Figure 10:
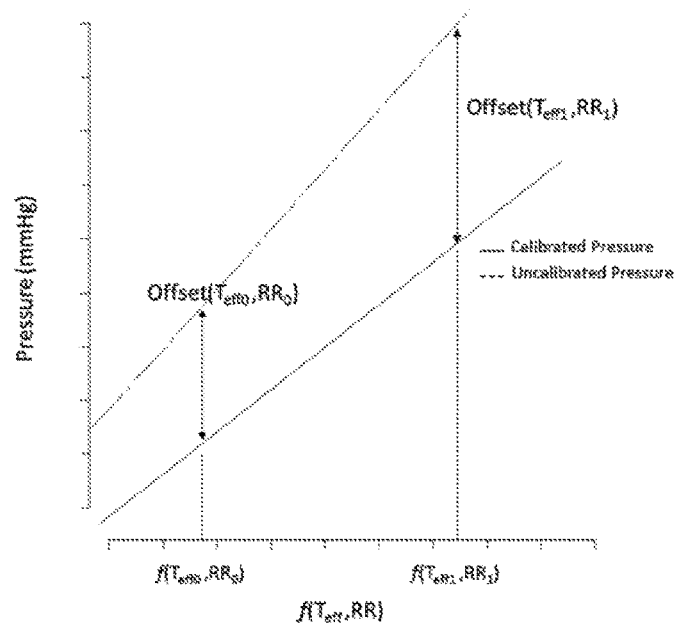
FIG. 10 contains a graph illustrating blood pressure estimation using the multivariable single hypothesis multi-point calibration model.

For all the aforementioned approaches, it was also considered a multi-point calibration. In this case, the offset is not a constant, but a function of the involved variables. The behavior of this modification is qualitatively depicted in FIGS. 9 and 10.

4. MULTIPLE BEATS SIGNAL PROCESSING AND FEATURES EXTRACTION

In ambulatorial scenarios, the noise can make it difficult to extract the characteristic points of the signal waves correctly, even after filtering and heavy signal processing. One approach that can increase the accuracy of the method in these circumstances is combining the signals of several heartbeats into one representative heartbeat that is, then, analyzed. This extra preprocessing step is appended just after the first step of FIG. 3. The new flow of the method, with this extra step, is presented in FIG. 11.

In the first step, the system accumulates samples from both the Electrocardiogram (ECG) and Plethysmography (Pleth) signals for a predefined period, usually longer than five heartbeats. The preprocessing occurs as described, using morphological and forward-backward filters to remove some of the noise.

After the first step, a preliminary analysis is performed over the acquired ECG signal window to extract the period of the signal (P, in samples) and to define characteristic points that can be used as trigger points in the next step. Usually, the peaks of the R wave are selected as these trigger points and are used to identify the period, but any well-defined point in the ECG signal may be selected. This preliminary analysis employs MMD transformed based analysis [4] or wavelet transforms [3] to identify the ECG trigger points.

After the trigger points are identified, the ensemble average technique is employed to reduce even more the noise from the signals and, at the same time, enhance their characteristic points. The ensemble average works as follows. For each one of the N trigger points identified, we define a frame, $x_i$, comprising P adjacent samples of the signal window, centered on the $i^{th}$ trigger point. N frames can be defined this way, each one with P samples. The ensemble average window, y, of length P, is created from the N frames using the formulation presented in equation 16.

$$y[k] = \frac{\sum_{i=1}^{N} x_i[k]}{N}, \quad k \in [1, P] \quad (16)$$

Since the Pleth and the ECG signals are synchronized the trigger points and the ECG period (P samples), previously identified, can be used for both the ECG and the Pleth signals.

The Features Extraction process (second step of FIG. 11) is performed as described before. However, instead of using the processed signal windows, the calculations are performed over the condensed versions of the Pleth ($y_{pleth}$) and the ECG ($y_{ECG}$) signals, created using the ensemble average technique (Equation 16).

5. BOUNDS ON SIGNAL FEATURES

Figure 11:
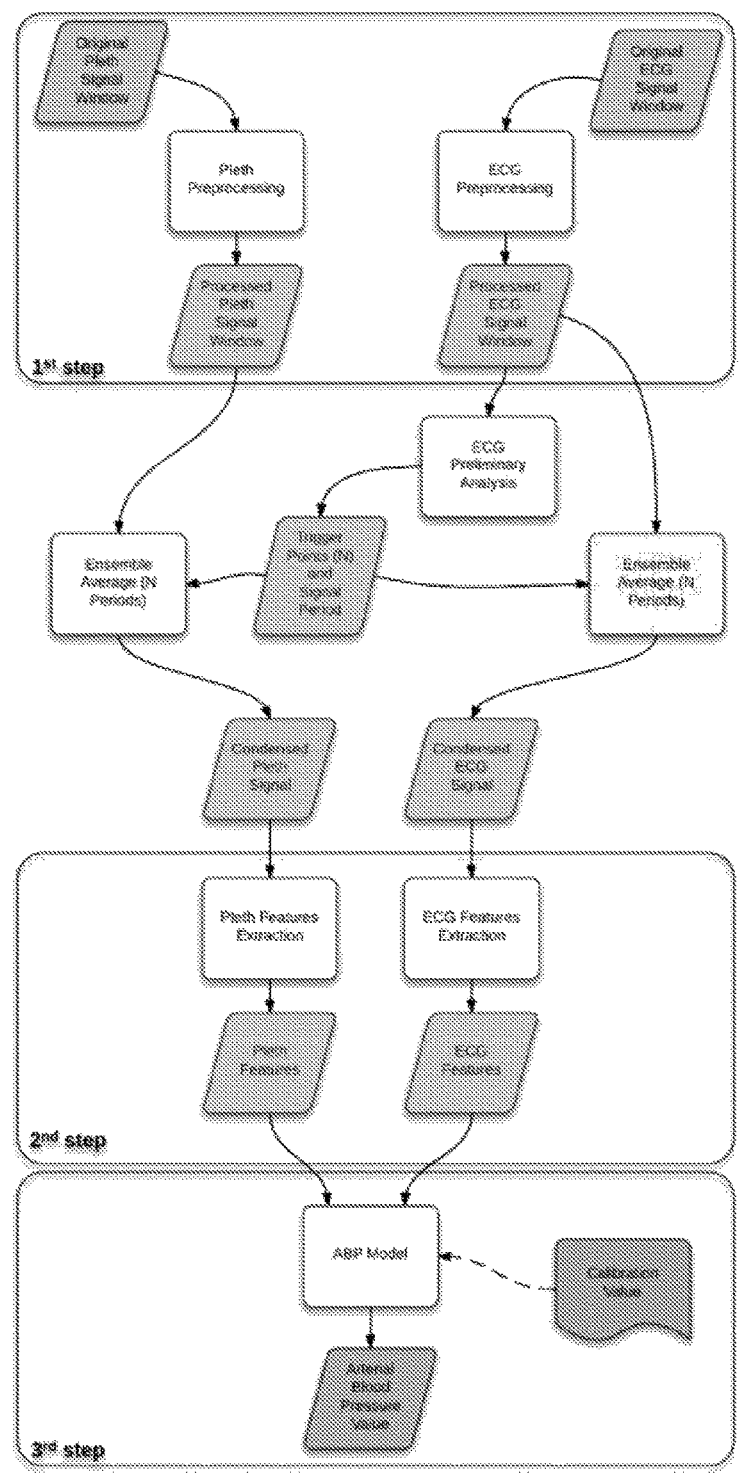
FIG. 11 gives an overview of the complete inventive method.

In non-controlled environments, even after all the already described processing, the results provided by the second step of FIGS. 3 and 11 may not be useful to the ABP model. This happens especially in ambulatorial scenarios, when the characteristics of the noises the system would be subject to are difficult to predict.

To reduce the incidence of these wrong values in the calculations, a simple check was designed for each of the extracted features. Using these sanity checks, the results presented by the system are more reliable.

With respect to the ECG, the RR interval value is bounded to the range [$RR_{Min}$, $RR_{Max}$], where both $RR_{Min}$ and $RR_{Max}$ are configurable. If the extracted value is outside this range, the signal is considered to be corrupted and the analysis window is discarded. When the ensemble average technique is used, it is expected that the window analyzed on the third step of FIG. 11 contains only one heartbeat. Therefore, if more than one R wave peak or S peak is detected, the window is also discarded. The intervals between the R peaks, S peaks and the zero-voltage crossing points are also checked to assure they are into proper range. The interval between the foot and the peak of the Pleth signal is also checked. If this interval is too long, the window is discarded.

Last, the interval between the zero-voltage crossing point and the Pleth wave is checked. If such interval is too long or too short, the window is discarded and the calculation of the ABP value is postponed until the processing of a valid window.

REFERENCES

[1]—Zhongguo Liu; Jinliang Wang; Boqiang Liu, "ECG Signal Denoising Based on Morphological Filtering," Bioinformatics and Biomedical Engineering, (iCBBE) 2011 5th International Conference on, vol., no., pp. 1, 4, 10-12 May 2011.

[2]—Oppenheim, A. V., and R. W. Schafer, Discrete-Time Signal Processing, Prentice-Hall, 1989, pp. 284-285.

[3]—Cuiwei Li; Chongxun Zheng; Changfeng Tai, "Detection of ECG characteristic points using wavelet transforms," Biomedical Engineering, IEEE Transactions on, vol. 42, no. 1, pp. 21, 28, January 1995

[4]—Yan Sun; KapLuk Chan; Shankar Muthu Krishnan, "Characteristic wave detection in ECG signal using morphological transform", BMC Cardiovascular Disorders, vol. 5, no. 1, September 2005

[5]—Mallat, S.; Zhong, S., "Characterization of signals from multiscale edges," Pattern Analysis and Machine Intelligence, IEEE Transactions on, vol. 14, no. 7, pp. 710, 732, July 1992

[6]—Cohen, A.; Kovacevic, J., "Wavelets: the mathematical background," Proceedings of the IEEE, vol. 84, no. 4, pp. 514, 522, April 1996

[7]—Rincón, F.; Recas, J.; Khaled, N.; Atienza, D., "Development and Evaluation of Multilead Wavelet-Based ECG Delineation Algorithms for Embedded Wireless Sensor Nodes," Information Technology in Biomedicine, IEEE Transactions on, vol. 15, no. 6, pp. 854, 863, November 2011

[8]—Dimosthenis Mayrilas; Theodora Tsapikouni; Dimitrios Mikroulis; Grigorios Nitzikas; Vassilios Didilis; Kosmas Tsakiridis; Fotis Konstantinou; Georgios Bougioukas, "Dynamic Mechanical Properties of Arterial and Venous Grafts used in Coronary Bypass Surgery", Journal of Mechanics in Medicine and Biology, Volume 02, no. 03, September 2002.

The invention claimed is:

1. A wrist-worn device for measuring blood pressure of a user, comprising:
    at least one of a back dial and a back side of a strap of the wrist-worn device configured to be in contact with an arm of the user on which the wrist-worn device is intended to be worn;
    an electrocardiogram (ECG) circuit with at least two electrodes, the ECG circuit configured to obtain an electrical activity of a heart of the user by measuring an ECG waveform detected by the at least two ECG electrodes;
    a pulse oximeter configured to obtain a pulse waveform corresponding to a blood flow in a blood vessel of the user; and
    a computing device configured to compute blood pressure using the ECG waveform and the pulse waveform, wherein the computing device uses a zero-voltage crossing point of the ECG waveform and a corresponding point on the pulse waveform, wherein the zero-voltage crossing is a point of the ECG waveform following a ORS complex when the ECG waveform has a zero-voltage value,
    wherein one or more of the at least two ECG electrodes is placed on at least one of the back dial and on the back side of the strap, and one or more of the at least two ECG electrodes is placed on a front side of the wrist-worn device or on a front side of the strap and is configured to be touched by the user,
    wherein the pulse oximeter includes an optical sensor operably connected to the pulse oximeter, the optical sensor being placed either on the at least one of the back dial and the back side of the strap, or on the front side of the device or on the front side of the strap in a proximity of the one or more of the at least two ECG electrodes,
    wherein the proximity is configured such that an intended touch by the user of the one or more of the at least two ECG electrodes causes the optical sensor to be touched simultaneously, and
    wherein the ECG circuit and the pulse oximeter are configured to simultaneously measure the ECG waveform and the pulse waveform.

2. A system for measuring blood pressure of a user comprising:
    an electrocardiogram (ECG) circuit with at least two ECG electrodes configured to obtain an electrical activity of a heart of the user by measuring an ECG waveform detected at the at least two ECG electrodes; and
    a pulse oximeter configured to obtain a pulse waveform corresponding to a blood flow of a vessel of the user; and
    a processor that is in electrical contact with the ECG circuit and the pulse oximeter,
    wherein the processor is configured to simultaneously analyze the ECG waveform and the pulse waveform, and
    wherein the processor is further configured to identify a zero-voltage crossing point of the ECG waveform, to determine time delays from the zero-voltage crossing point to respective different determined points of the pulse waveform, and to use the time delays to compute blood pressure values of the user,
    wherein the zero-voltage crossing point is a point of the ECG waveform following a ORS complex when the ECG waveform has a zero-voltage value.

3. A method for measuring blood pressure comprising steps of:
    analyzing an electrocardiogram (ECG) waveform and a pulse waveform obtained from an ECG circuit and a pulse oximeter, respectively;
    identifying a zero-voltage crossing point, wherein the zero-voltage crossing point is a point of the ECG waveform following a ORS complex when the ECG waveform has a zero-voltage value;
    determining time delays from the zero-voltage crossing point to different determined points of the pulse waveform; and
    calculating the blood pressure based on a function of the time delays.

4. The method of claim 3, wherein the step of determining time delays further comprises:
    measuring an effective time delay $T_{eff}$ from the zero-voltage crossing point to a steepest point of the pulse waveform.

5. The method of claim 3, wherein the step of determining time delays further comprises:
    measuring an effective time delay $T_{eff}$ from the zero-voltage crossing point to a peak of the pulse waveform.

6. The method of claim 3, wherein the ECG waveform and the pulse waveform are offset by one or more electrocardiogram beats from each other.

7. The method of claim 3, further comprising the step of:
    merging multiple ECG waveform beats from the ECG waveform into a single beat for analysis, the merging providing for an ensemble average of the multiple ECG waveform beats.

8. The method of claim 3, further comprising the step of:
    merging multiple pulse waveform beats from the pulse waveform into a single beat for analysis, the merging providing for an ensemble average of the beats.

9. The method of claim 3, wherein the step of identifying the zero-voltage crossing point includes:
    computing a dyadic discrete wavelet transform of the electrocardiogram for different wavelet scales;
    determining a peak of an R waveform by searching for pairs of maximum moduli of opposite signals across scales that exceed predefined thresholds;
    determining a peak of an S waveform by searching for pairs of maximum moduli of opposite signals at a chosen scale, chronologically after the peak of the R waveform in a neighborhood of the peak of the R waveform; and
    determining the zero-voltage crossing point by searching a maximum modulus associated to a last slope of a QRS complex at a chosen scale for a value that is lower than a predefined threshold.

10. The method of claim 3, wherein the step of identifying the zero-voltage crossing point includes:
    computing a Multiscale Morphological Derivative (MMD) transform of the ECG waveform;
    detecting peaks of R waveforms by searching for minima that exceed a predefined threshold value;
    determining peaks of S waveforms by searching for a first maximum chronologically after the peaks of the R waveforms; and defining the zero-voltage crossing point as a first local minimum chronologically after the peaks of the S waveforms.

11. The method of claim 3, wherein the step of calculating the blood pressure values includes:
computing, based on multiple functions of the time delays from the zero-voltage crossing point to the pulse waveforms, specific ranges of RR intervals of the ECG waveform, with a particular function chosen based on a corresponding RR interval of the ECG waveform.

12. The method of claim 3, further comprising the steps of:
computing the blood pressure values using an existing blood pressure device, along with a measurement of the time delays from the zero-voltage crossing point of the ECG waveform to the pulse waveform; and
building an offset function that relates the blood pressure values; and
adjusting a function mapping of the time delays and the blood pressure values based on the offset function to perform a pre-calibration step.

13. The method of claim 12, wherein the offset function is computed to include a plurality of offset functions, each one for a specific range of RR intervals of the ECG waveform, with a particular function chosen based on a corresponding RR interval of the ECG waveform.

14. The method of claim 3, wherein the step of determining the time delays further calculates the time delays as an average of different values across different leads of the ECG waveform.

15. The method of claim 3, further comprising the step of:
determining different leads of the ECG waveform and combining the different leads by an averaging function.

16. The method of claim 3, further comprising the step of:
determining different leads of the ECG waveform and performing a root mean square (RMS) of the different leads.

17. The method of claim 11, wherein an ECG waveform single beat is discarded if the RR interval of the ECG waveform is outside a pre-defined threshold value.

18. The method of claim 11, wherein a pulse waveform single beat is discarded if the RR interval of the ECG waveform is outside a pre-defined threshold value.

19. The method of claim 11, further comprising the step of:
discarding a beat and corresponding pulse waveform when computing an ensemble average, if more than R or S waveform of ECG waveform is detected at the beat.

20. The method of claim 11, further comprising the step of:
checking intervals between the R peaks, S peaks and the zero-voltage crossing points to see whether the intervals fall within a predefine range, and if not, discarding corresponding ECG beat and pulse waveforms when computing an ensemble average.

21. The method of claim 3, further comprising the step of:
determining whether time intervals between the zero-voltage crossing point and the different determined points of the pulse waveform do not fall within pre-defined ranges, and if the time intervals do not fall within the predetermined ranges, the step of calculating the blood pressure is not performed and postponed until the time intervals fall within predefined ranges.

22. The method of claim 11, further comprising the step of:
determining whether time intervals between the zero-voltage crossing point and the different determined points of the pulse waveform do not fall within pre-defined ranges, and if the time intervals do not fall within the predetermined ranges, discarding corresponding ECG beat and pulse waveforms when computing an ensemble average.

* * * * *